United States Patent [19]  [11] 4,412,823
Sakai et al. [45] Nov. 1, 1983

[54] ORAL CAVITY CLEANER

[75] Inventors: Hiroaki Sakai; Tadanori Okazaki, both of Fukuoka, Japan

[73] Assignee: Matsushita Electric Industrial Co., Ltd., Osaka, Japan

[21] Appl. No.: 281,926

[22] Filed: Jul. 10, 1981

[30] Foreign Application Priority Data

Jul. 21, 1980 [JP] Japan ................................. 55-100400

[51] Int. Cl.³ ............................................ A46B 13/06
[52] U.S. Cl. ........................................ 433/80; 128/66
[58] Field of Search ................. 433/80; 128/66, 62 A, 128/50; 132/11 A, 84 R

[56] References Cited

U.S. PATENT DOCUMENTS 3,214,775 11/1965 Murov et al. ........................... 128/66
3,547,110 12/1970 Balamuth ............................... 128/66
3,590,813 7/1971 Roszyk .................................. 128/66
3,771,186 11/1973 Moret et al. ........................... 128/66
3,909,867 10/1975 Hogsell ................................. 433/80
4,257,433 3/1981 Kwan ................................. 132/84 R

*Primary Examiner*—Jay N. Eskovitz
*Attorney, Agent, or Firm*—Spencer & Kaye

[57] ABSTRACT

An oral cavity cleaner including a pump unit for supplying a pulsating stream of high-pressure fluid, and a toothbrush unit connected thereto via a flexible conduit. The toothbrush unit includes an actuating member responsive to the pressure of the pulsating stream of fluid to provide a reciprocatory movement, a toothbrush connected to the actuating member, a valve section brought to an open position when the movement of the actuating member has exceeded a predetermined value, and an operating member for operating the valve section. The toothbrush can be automatically given a reciprocatory movement, and the high-pressure fluid can be ejected through the toothbrush or its ejection can be stopped as desired by manipulating the operating member while the toothbrush is being moved with a reciprocatory movement.

11 Claims, 11 Drawing Figures

ORAL CAVITY CLEANER

BACKGROUND OF THE INVENTION

The present invention relates to an oral cavity cleaner for driving a toothbrush and simultaneously injecting a water jet by means of a stream of pulsating high-pressure fluid to remove sordes and foreign matter from teeth for prevention of tooth decay and to massage the gums for effective, timesaving prevention and treatment of pyorrhes alveolaris.

Generally, there are two types of oral cavity cleaners, one of which are toothbrushes, and the other of which are devices for injecting through tips of nozzles high-pressure water discharged from pump devices. Toothbrushes are easy to handle and are effective for removing sordes, but are deficient in construction since it is difficult to reach gaps between the teeth, thereby leaving therein sordes and foreign matter. On the other hand, the devices for injecting high-pressure water are good for removing foreign matter such as food crumbs jammed in the gaps between the teeth and between the teeth and gum, and for promoting circulation of the blood in the gums by means of a pulsating jet, resulting in effective prevention and treatment of pyorrhes alveolaris. However, high-pressure water injecting devices are insufficient for removing sordes adhered to surfaces of the teeth.

The two devices of the prior art have both merits and demerits as aforesaid. It is essential, as seen in reports made at the meetings of the Oral Hygienic Society, that the two devices be used in combination to achieve satisfactory results in cleaning the oral cavity. However, it is not only time consuming but also troublesome to use the two devices in combination. When toothbrushes are manually operated, there are individual differences in the results achieved in cleaning the oral cavity and hands becomes tired. To obviate these disadvantages, automatic motor-operated toothbrushes are commercially available nowadays. This type of toothbrushes must be used in combination with high-pressure water injecting devices to achieve satisfactory results in cleaning the oral cavity, so that they do not contribute much to the saving of time and to the elimination of a troublesome operation in cleaning an oral cavity. Furthermore, the provision of such expensive articles as motor-operated toothbrushes and high-pressure water injecting devices makes an economic burden for average homes.

Toilet alcoves in households are narrow and the space for storing such articles is relatively small, so that one would experience inconvenience in using such articles. Proposals have hitherto been made to combine a high-pressure water injector and an electrically-operated toothbrush into a single device, and to combine a hydraulically-operated toothbrush with a high-pressure water injector into a single device. In these devices, it is necessary to provide a pick for a nozzle for injecting high-pressure water and a toothbrush separately and to interchangeably use them, to increase the effects they achieve in cleaning the oral cavity. It is not only time consuming but also troublesome to attach and detach these parts, so that the devices would be low in efficiency. This would result in the users only using one of the two parts and consequently the devices would be unable to attain the end of performing two functions.

Another important disadvantage would be that if the high-pressure water injector alone is used and the toothbrush is not used, the devices would be of no avail in preventing decay of the teeth because removal of sordes on the teeth could not be accomplished with sufficient effectiveness. In view of this disadvantage, devices which make it necessary to interchangeably use a toothbrush and a pick do not achieve the effects for which they are intended, because they impose an economic burden on the users and cause unnecessary trouble. Further, it has been found that most prospective users can be thoroughly familiarized with the way of using these devices. It would be apparent that this would raise the problem that the users of these devices might suffer from diseases of the teeth in spite of using them.

SUMMARY OF THE INVENTION

This invention has been developed for the purpose of obviating all the aforesaid disadvantages of the prior art. An object of the invention is to provide an oral cavity cleaner capable of achieving in a short period of time the effects of cleaning the oral cavity and massaging the gum satisfactorily.

Another object is to provide an oral cavity cleaner of a construction which enables most users to positively brush the teeth with a toothbrush and to positively remove sordes and foreign matter from the teeth while massaging the gums with a pulsating stream in the form of a jet of water.

Still another object is to provide an oral cavity cleaner which causes no trouble or inconvenience to most users and enables them to achieve better results in a short time in cleaning the oral cavity with efficiency and ease than the devices of the prior art.

Still another object is to provide an oral cavity cleaner capable of contributing greatly to the development of oral cavity hygiene by offering the aforesaid advantages.

The outstanding characteristic of the invention is that the oral cavity cleaner comprises an on-off valve located at a toothbrush unit for turning on and off, as desired, a pulsating stream in the form of a jet ejected through a toothbrush while the latter is being moved in a swinging movement.

DESCRIPTION OF THE PREFERRED EMBODIMENT

Figure 1:
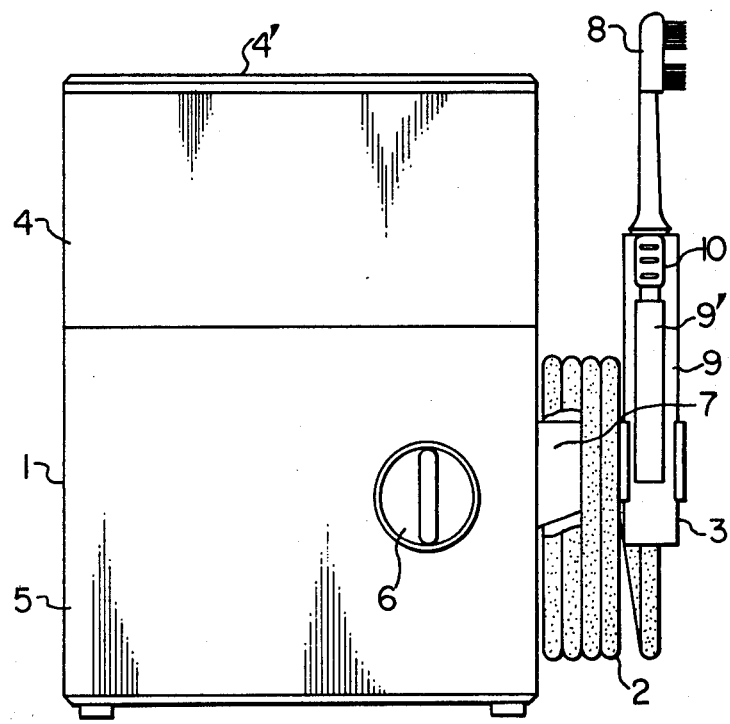
FIG. 1 is a front view of an oral cavity cleaner according to one embodiment of the invention.

FIG. 1 shows the external appearance of the oral cavity cleaner according to the invention. As shown, a pump unit 1 for producing a pulsating stream of high-pressure water is connected to a toothbrush unit 3 via a single flexible conduit 2 for providing a passage for the pulsating stream of high-pressure water flowing back and forth between the pump unit 1 and the toothbrush unit 3. The pump unit 1 comprises a fluid container or water tank 4, and a pump and a drive section housed in a case 5 having a knob 6 for actuating a power source switch, and a support 7 for the flexible conduit 2 and toothbrush unit 3. The water tank 4 is provided at its top with a lid 4' which keeps the water tank 4 clean when not in use. The toothbrush unit 3 has detachably attached thereto a toothbrush 8 adapted to eject a pulsating stream in the form of a jet. In use, the flowrate of the pulsating jet stream is preferably adjusted. To this end, the pump in the case 5 is provided with flowrate control means coupled to the knob 6 to control the flowrate.

The toothbrush unit 3 further comprises a case 9, and an operating member 10 disposed at an upper portion of the case 9 near the toothbrush 8. By actuating the operating member 10, the pulsating jet stream ejected through the toothbrush 8 can be stopped as desired during use.

In operation, the toothbrush 8 is attached to the toothbrush unit 3 and the knob 6 is turned to turn on the power source switch after the water tank 4 is filled with water. The pump unit 1 produces a pulsating jet stream which is fed through the flexible conduit 2 to the toothbrush unit 3, to thereby operate the toothbrush 8.

By actuating the operating member 10, it is possible to operate the toothbrush 8 while allowing the pulsating jet stream to be ejected. Thus the toothbrush 8 and the high-pressure water jet can both be simultaneously actuated to perform their respective functions, that is, to permit the cleaning effect and the massaging effect to be achieved as desired. Cleaning effects can be achieved merely by using water as a jet stream. However, the use of a liquid tooth cleaning agent added to the pulsating jet stream would let the user feel greatly refreshed after using the cleaner. When the user wishes to use a toothpaste according to custom, the supply of the pulsating jet stream can be interrupted by means of the operating member 10, so that the toothbrush 8 can be used without any water being ejected therethrough. Thus the user can operate the toothbrush 8 in the same manner as an electrically-operated toothbrush of the prior art, and the pulsating jet stream can be ejected through the toothbrush 8 by actuating the operating member 10 again. The invention thus enables most users to be benefited from the cleaning and massaging operations positively and readily without any trouble. The swinging movement of the toothbrush 8 and the intensity of the pulsating jet stream ejected through the toothbrush 8 can be controlled by means of the knob 6, to enable operation of the cleaner to suit the conditions of the teeth and gums of the user. More specifically, the swinging movement of the toothbrush 8 and the intensity of the pulsating jet stream can be simultaneously switched between high and low. This allows the user to reduce both the swinging movement of the toothbrush 8 and the intensity of the pulsating jet stream in use. When the user wishes to use the toothbrush 8 by moving it in a vigorous swinging movement while causing an intense pulsating jet stream to be ejected through the toothbrush 8, this end can be attained without any trouble. Thus the oral cavity cleaner according to the invention is constructed to meet the requirement of any user depending on the conditions of the teeth and gums, so that the objects of achieving excellent cleaning and massaging effects can be accomplished positively and readily.

The embodiment of the invention shown in FIG. 1 will now be described in detail by referring to the drawings.

Figure 2:
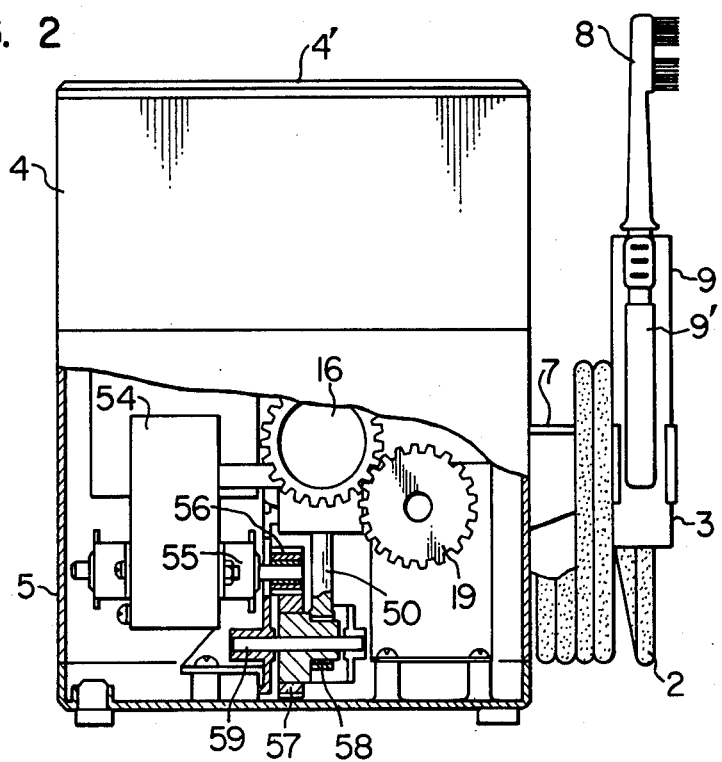
FIG. 2 is a sectional side view of the pump drive section of the oral cavity cleaner shown in FIG. 1.
Figure 4:
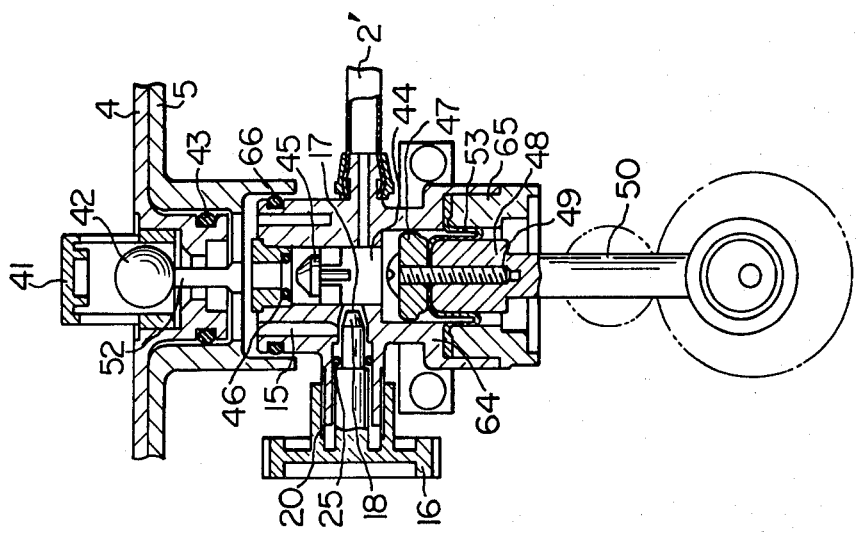
FIGS. 3 and 4 are sectional views of the pump section of the oral cavity cleaner shown in FIG. 1.
Figure 3:
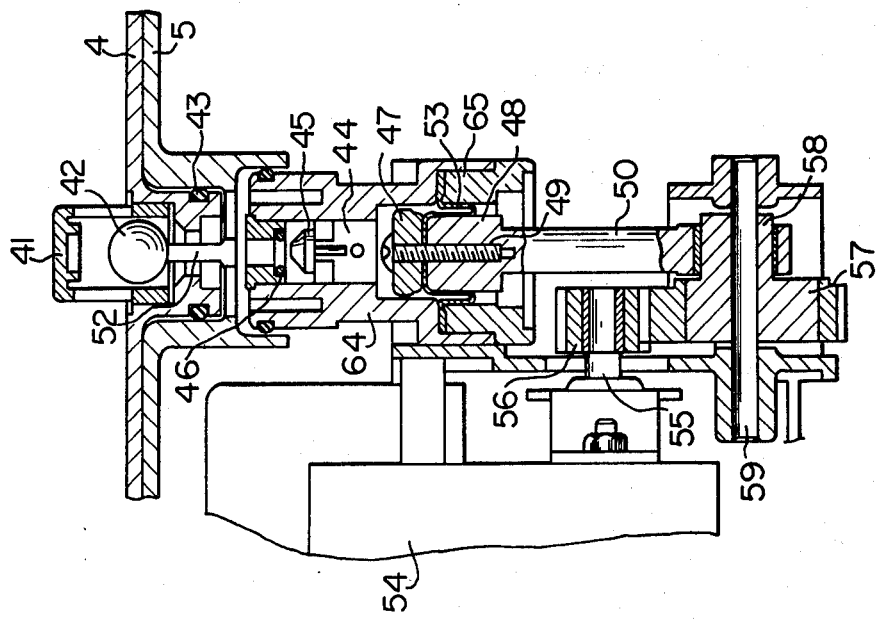
Figure 6:
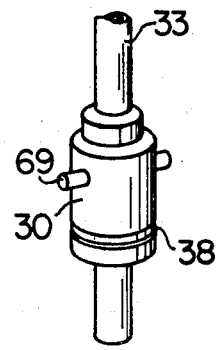
FIG. 6 is a perspective view of the actuating piston.
Figure 7:
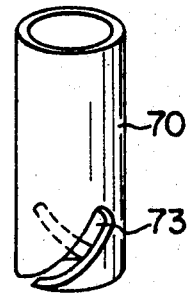
FIG. 7 is a perspective view of the spiral guide.

FIGS. 2-4 shows the construction of the pump unit 1. The water tank is provided at a water feeding section with a filter 41 for filtering any foreign matter that might be incorporated in the cleaning water in the tank 4, and a valve 42 for avoiding leakage at the time of feeding the water. By attaching the water tank 4 to the upper portion of the case 5, it is possible to cause the cleaning water to flow into a pump chamber 44 as a valve pusher 52 of the case 5 pushes the valve 42 upwardly. A seal 43 is provided between the water tank 4 and the case 5 to avoid leakage.

The pump chamber 44 has a piston section comprising a piston rod 50 having a mounting portion 48 at its forward end, and a piston valve 53 formed of a resilient material in the form of a bellowsphragm having folds, for example, secured by a screw 49 to the mounting portion 48 while being held in place by a retainer plate 47 serving concurrently to prevent the piston valve 53 from becoming eccentric. The retainer plate 47 is maintained in light contact with a pump case member 64 to avoid its becoming concentric, so that the piston valve 53 is capable of enduring repeated operations and consequently can have a prolonged service life. The piston valve 53 is held between pump case members 64 and 65 to constitute a part of the pump chamber 44.

A drive motor 54 has its torque increased by a drive pinion 56 and a follower gear 57 secured to a shaft 55, to a value corresponding to the reduction ratio. The aforesaid piston section is moved in reciprocatory movement by an eccentric portion 58 rotating simultaneously with the follower gear 57 and eccentric with respective to a center shaft 59, with a stroke which is twice the amount of eccentricity. Linked to the movement of the piston section is the movement of a check valve 45 which moves up and down to generate a pulsating pressure in the pump chamber 44 to supply a pulsating jet stream to the toothbrush unit 3 via the flexible conduits 2' and 2. More specifically, when the water is drawn into the pump chamber 44, the check valve 45 moves downwardly to allow the cleaning water to flow into the pump chamber 44 through a clearance between the check valve 45 and a valve seat 46. When the cleaning water is discharged from the pump chamber 44, the check valve 45 moves upwardly into sealing engagement with the valve seat 46, to allow the pressurized cleaning water to be exhausted through the flexible conduit 2'. This process is repeated to supply a pulsating stream of high-pressure water to the toothbrush unit 3 through the flexible conduits 2' and 2.

In the embodiment shown and described hereinabove, the speed of the drive motor 54 is reduced by one stage. Considering the influences of the toothbrush on the teeth and the gums, the results achieved in cleaning and the utility of the device, the swinging movements of the toothbrush preferably have a frequency of about 2000 cycles per minute at most. To meet the requirement of conserving energy, the invention provides a combination of the drive motor 54 with a speed reducing mechanism of a suitable reduction ratio, to set the number of strokes and the torque of the piston section at appropriate values.

The flow rate control mechanism provided to the pump unit 1 will be described in detail. The pump case 64, 65 is formed with a bypass 15 (FIG. 4) for the pulsating fluid in the pump chamber 44 which connects the pump chamber 44 with a flow passage connected to an inlet port disposed above the valve seat 46. The bypass 15 has fitted therein a valve body 16 threadably fitted over an externally threaded portion 20 formed on the outer periphery of a projection from the pump case member 64 and having an O-ring 25 between the inner periphery of the projection and the valve body 16. A taper valve 18 located at one end of the valve body 16 and a valve seat 17 of the pump case member 64 constitute a flowrate control valve mechanism.

To effect flowrate control, the knob 6 is turned to rotate a drive gear 19 (FIG. 2) linked thereto and meshing with the valve body 16 through a threaded portion at its outer periphery, so that the valve body 16 moves in sliding movement by virtue of the threadable engagement with the externally threaded portion 20, to thereby vary the size of a clearance formed between the taper valve 18 and the valve seat 17. More specifically, in the embodiment shown and described hereinabove, the drive gear 19 has directly connected to its shaft a power source switch, and the valve body 16 is in meshing engagement with the drive gear 19 in such a manner that the aforesaid clearance has its size maximized when the power source switch is turned off and the pump unit 1 is inoperative. By turning the knob 6 to turn on the power source switch and further turning the knob 6, the valve body 16 is moved in sliding movement by the aforesaid mechanism to gradually reduce the size of the clearance, until the taper valve 18 abuts against the valve seat 17 and the bypass 15 is blocked. Thus the flowrate of the pulsating stream of fluid supplied from the pump chamber 44 through the flexible conduits 2' and 2 to the toothbrush unit 3 can be controlled in such a manner that the flowrate is minimized when the power source switch is turned on and gradually increased as the knob 6 is turned until it is maximized. The pressure of the pulsating stream of fluid is varied as the flowrate thereof through the bypass 15 is varied. It is to be understood that there is no interference with the operation of the toothbrush unit 3 presently to be described so long as the valve section and the bypass 15 have their specifications appropriately set. Thus the oral cavity cleaner according to the invention is capable of having the swinging movement of the toothbrush and the intensity of the pulsating jet stream adjusted from high to low as aforesaid, so that the cleaner can be made to suit the conditions of the teeth and gums and the taste of most users.

The toothbrush unit 3 will now be described in detail as to its construction and operation by referring to FIGS. 5–8. The toothbrush unit 3 has a liquid or fluid pressure actuating section, a motion transmitting member 33 and a motion converting section (subsequently to be described) built therein. The liquid pressure actuating section is responsive to the pressure of the pulsating stream of fluid supplied through the flexible conduit 2 to a chamber 10' from the pump unit 1, to drive the motion transmitting member 33, and the toothbrush 8 fitted to the member 33. The liquid pressure actuating section comprises a cylinder 28, an actuating piston 30, and a seal 38 mounted on the piston 30 and abutting against the cylinder 28.

The actuating piston 30 has a pressure receiving surface 71 that partly defines the chamber 10' which is also partly defined by a joint member 12 having a fluid or water passage 14 formed therein and connected at one end through a member 13 to the flexible conduit 2. A seal 11 is mounted between the joint member 12 and the case 9 so as to fix the joint member 12 to the case 9. The actuating piston 30 has a seal 38 fitted thereto and moves in sliding movement along the inner wall surface of the cylinder 28 which includes an arbitrarily selected sliding member as a separate piece and is fitted to and held by the case 9 through an O-ring 39.

The motion transmitting member 33 formed with an axially extending water passage 34 is attached substantially coaxially to the actuating piston 30 and fitted at its lower portion in a bearing section 24, to hold the actuating piston 30. The motion transmitting member 33 is formed at its lower end with an inlet port 27 providing a valve seat which cooperates with a valve body 29 adapted to be brought into and out of contact with the valve seat, to constitute a valve for the passage of water from the chamber 10' to the water passage 34. The motion transmitting member 33 has fitted at its upper end through an O-ring 37 the toothbrush 8 formed with a water passage 35 and a nozzle 35'. There is also provided an operating section for opening and closing the valve section.

The operating section comprises an operating member 32 supported for vertical sliding movement between the case 9 and a guide plate 9' which has an operating knob in the upper portion of the case 9 on the side of the toothbrush 8 and a rack portion 32' in the lower portion of the case 9, and a valve body locking member 26 having a pinion 40 engaging the rack portion 32' and supported by the case 9 through its drive shaft inserted into the case 9 through an O-ring 31.

Figure 5:
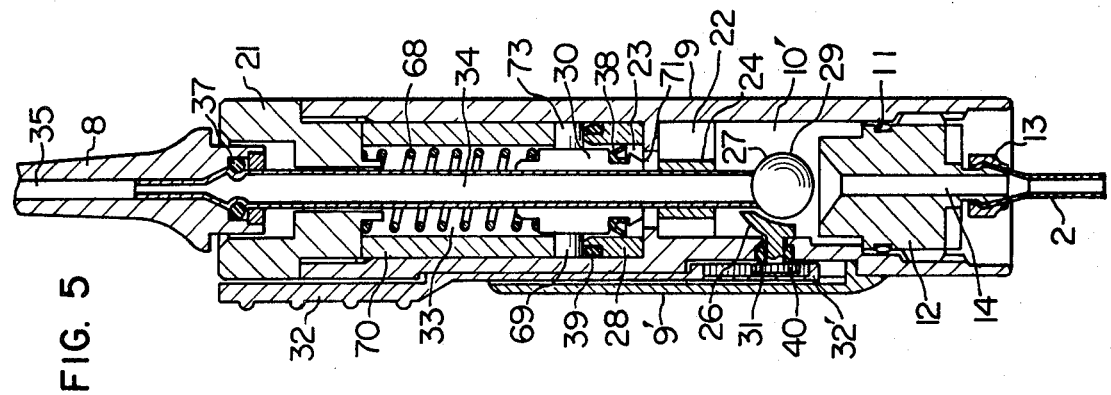
FIG. 5 is a sectional view of the toothbrush unit of the oral cavity cleaner shown in FIG. 1.

The valve body locking member 26 locks the valve body 29, when it is in the condition shown in FIG. 5. That is, the valve section is in an 'open' position. Downward movement of the operating member 32 causes the locking member 26 to rotate through substantially 90° by virtue of the meshing engagement of the rack portion 32' with the pinion 40. Thus the valve body 29 and the locking member 26 are relatively positioned with respect to each other in such a manner that the center axis of the actuating piston 30 is disposed perpendicular to the plane of FIG. 5, so that the valve body 29 is released from locking engagement with the locking member 26 and the valve section is brought to a 'closed' position. Meanwhile the actuating piston 30 is urged by the biasing force of a spring 68 mounted between a support member 21 and the actuating piston 30 to move toward the chamber 10' into which the pulsating stream of fluid is introduced. This enables the actuating piston 30 to be quickly restored to its original position when the pressure of the pulsating stream produced in the chamber 10' is removed therefrom. As the knob 6 is turned to turn on the power source switch, the pulsating stream of fluid is supplied by the pump unit 1 through the flexible conduit 2 to the toothbrush unit 3. That is, the water passage 14 and chamber 10' are brought into communication with water passages 22 and a chamber 23, so that a force commensurate with the effective operation area of the pressure receiving section of the actuating piston 30 is exerted thereon. This causes the actuating piston 30 to move against the biasing load applied by the spring 68 to a position corresponding to the peak value of the pressure of the pulsating stream of fluid.

As described hereinabove, the actuating piston 30 is moved upwardly by the pressure of the pulsating stream of fluid. Thus when the actuating piston 30 is in the position shown in FIG. 5, the valve body 29 is locked by the locking member 26 and the inlet port 27 opens in the chamber 10', so that the pulsating stream is introduced from the chamber 10' into the inlet port 27 and flows through the flow passages 34 and 35 to the nozzle 35' of the toothbrush 8, from which it is ejected. When the valve section is brought to an 'open' position, it is possible to obtain ejection of the pulsating jet stream while the toothbrush 8 is being moved in a swinging motion.

On the other hand, when the valve section is brought to a 'closed' position, the valve body 29 is not restrained by the locking member 26. Thus the pressure of the pulsating stream of fluid acting in the chamber 10' applies to the actuating piston 30 a fluid force defined by the cylinder 28 and the seal 38, and to the valve body 29 a fluid force corresponding to the area thereof in contact with the inlet port 27 at the lower end of the motion transmitting member 33, so that the valve body 29 moves upwardly while being in abutting engagement with the inlet port 27.

The oral cavity cleaner can be operated as an electrically-operated toothbrush by bringing the valve section to the closed position. Since the pump unit 1 is provided with a flow rate control mechanism linked to the knob 6, it is possible to vary as desired the degree of the swinging movement of the toothbrush 8 and the volume (intensity) of the pulsating jet stream ejected through the toothbrush 8.

By selecting a suitable spring constant for the spring 68, it is possible to actuate the actuating piston 30 not only by producing a positive and negative pressure of the sine cycle in the pulsating stream but also by reducing the negative pressure to a low level as compared with the positive pressure, while the pulsating stream is under a periodically changing pressure. It is also possible to bring the pressure in the chamber 10' substantially to a positive level when the actuating piston 30 is restored to the original position, by the biasing force of the spring 68. That is, the spring 68 has not only the function of accelerating the return movement of the actuating spring 30 but also the pumping function of promoting the ejection of the pulsating stream through the nozzle 35' of the toothbrush 8.

Figure 11:
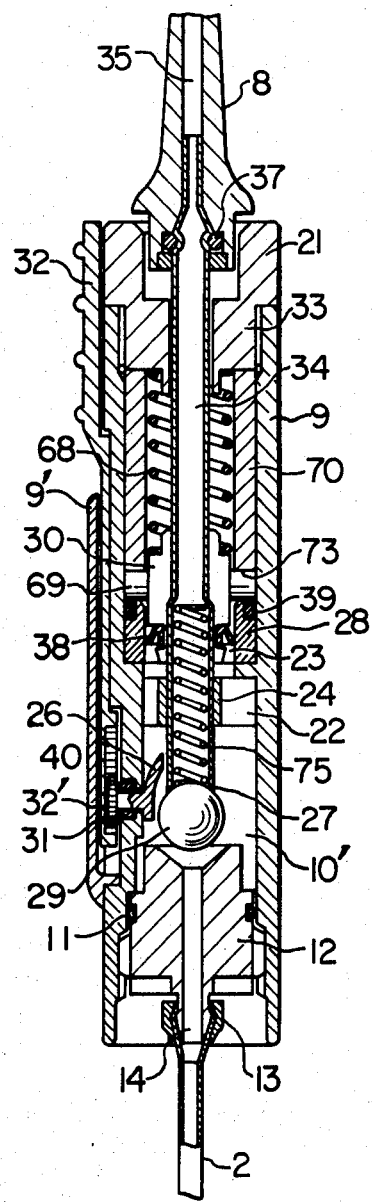
FIG. 11 is a sectional view of a modification of the toothbrush unit.
Figure 8:
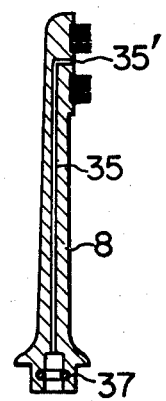
FIG. 8 is a sectional view of the toothbrush.
Figure 9:
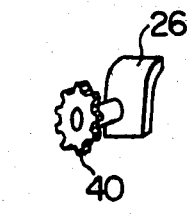
FIG. 9 is a perspective view of the valve body locking member.
Figure 10:
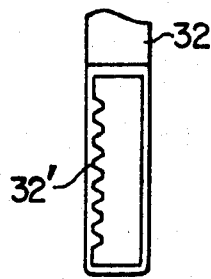
FIG. 10 is a side view of the operating member.

In the construction shown in FIG. 5, the clearance between the locking member 26 and the valve body 29 is small in size and it is possible to turn on and off a jet stream ejected through the nozzle 35' of the toothbrush 8 by means of the operating member 32. However, this entails a complicated operation for use. FIG. 11 shows a modification of the invention shown in FIG. 5 which provides improvements and increases the utility of the oral cavity cleaner.

As shown in FIG. 11, the clearance between the locking member 26 and the valve body 29 is greater in size in initial stages than in the embodiment shown in FIG. 5. By this feature, ejection of a jet stream through the toothbrush 8 is prevented when the toothbrush 8 alone is operated by turning the knob 6, without requiring the user to operate the operating member 32. More specifically, in the modification shown in FIG. 11, as the knob 6 is turned after the power source switch is turned on, the swinging angle of the toothbrush 8 is gradually increased while the ejection of a jet stream is prevented. This makes it possible to use the toothbrush 8 while adjusting its swinging angle by means of the knob 6, as is the case with an electrically-operated toothbrush of the prior art. Further rotation of the knob 6 increases the flow rate of the fluid introduced into the chamber 10' and raises the actuating piston 30, so that the valve body 29 also moves upwardly while being maintained in contact with the valve seat 27 of the piston 30. However, in the condition shown in FIG. 11, the valve section is brought to an 'open' position by the locking member 26, to enable the toothbrush 8 to be operated while allowing a jet to be ejected therethrough. A spring 75 has the function of quickly moving the valve body 29 downwardly when the valve section is in the open position. Ejection of a jet stream causes changes to occur in the movement of the actuating piston 30, so that it is possible to use the oral cavity cleaner by suitably controlling the movement of the piston 30 by means of the knob 6.

While using the toothbrush with ejection of a jet, it is possible to turn on and off the valve section by means of the operating member 32, in the same manner as described by referring to the embodiment shown in FIG. 5. In the modification shown in FIG. 11, it is possible to adjust the swinging angle of the toothbrush 8 functioning as an electrically-operated toothbrush by turning on the knob 6, and a jet is ejected through the toothbrush 8 after a certain range of swinging angle is exceeded. Thus it is only possible to turn on and off the jet stream in a swinging angle range exceeding the aforesaid certain range. For users who prefer to use a toothpaste according to custom, this offers the advantage that the order of adjusting the swinging angle of the toothbrush and the use thereof are standardized. This feature is distinct from the feature of the embodiment shown in FIG. 5 which enables a jet stream to be turned on and off at all times. In addition, the aforesaid motion converting section is provided between the liquid pressure actuating section and the motion transmitting member, to impart a reciprocatory spiral movement to the toothbrush 8.

The motion converting section includes a spiral guide 70, and members 69 for imparting a rotary movement to the actuating piston 30 and the movement transmitting member 33.

The members 69 for imparting a rotary movement to the actuating piston 30, which at least form a pair, are each engaged in one of guide grooves 73 forming a pair arranged spirally on the surface of the spiral guide 70, which is partially in abutting engagement with the cylinder 28 and held in place by the support member 21 located thereover. The cylindrical guide 70 serves concurrently as a guide for the spring 68. Since the members are forcedly engaged in the respective guide grooves 73, the toothbrush 8 attached to the motion transmitting member 33 connected to the actuating piston 30 inevitably moves in a spiral reciprocatory movement as the actuating piston 30 moves up and down.

From the foregoing description, it will be appreciated that according to the invention a pulsating stream of high-pressure fluid controlled to an arbitrarily selected flow rate by the flow rate control means connected to the knob is supplied from the pump unit 1 through the flexible conduit 2 to the toothbrush unit 3, and the toothbrush 8 is moved in a spiral reciprocatory movement by means of the liquid pressure actuating section and the motion transmitting section is responsive to the pressure of the pulsating stream of fluid while the latter is ejected through the nozzle 35' of the toothbrush 8. Thus the invention enables most users to enjoy, by a simple and reliable mechanism, the benefits of cleaning the teeth with a toothbrush, removing sordes and foreign matter from the teeth by a pulsating jet stream of water and massaging the gums by the pulsating stream. The device is free from trouble and inefficiency during operation and can be used readily and positively, to achieve the cleaning results in a short period of time. Thus the oral cavity cleaner according to the invention is convenient to use and reliable in performance, thereby contributing to the maintenance of the oral cavity in an excellent sanitary condition by effecting through cleaning.

In the invention, the swinging movement of the toothbrush and the intensity of a pulsating stream of fluid can be adjusted after the power source switch is turned on by turning a knob, and the jet stream ejected through the toothbrush 8 can be readily turned on and off by means of the operating member 32 of the toothbrush unit 3 while keeping the swinging movement of the toothbrush and the intensity of the jet in the controlled condition. Thus it is possible to temporarily stop the jet when the user desires to apply toothpaste to the toothbrush 8 or to remove the toothbrush unit 3 from the mouth.

The valve section according to the invention is highly effective in blocking the flow of fluid. The oral cavity cleaner according to the invention is simple in construction, compact in size, low in cost and high in efficiency during service, so that it contributes greatly to promoting the health of the users by efficiently cleaning the oral cavity.

What is claimed is:

1. An oral cavity cleaner comprising:
   a pump unit including
     a container for storing a fluid; and
     a pump coupled to said container for providing said fluid at high pressure;
   a flexible conduit; and
   a toothbrush unit coupled to said pump unit by means of said flexible conduit, said toothbrush unit including
     a toothbrush;
     a fluid pressure actuating section operated by the pressure of said high pressure fluid, said fluid pressure actuating section having an actuating member;
     a motion transmitting member having a fluid passage therein extending from said fluid pressure actuating section to said toothbrush, said motion transmitting member being driven by said fluid pressure actuating section and transmitting movement to said toothbrush;
     a valve section located within said fluid passage and including a valve body driven by the discharge pressure from said pump unit to close said fluid passage, said valve section being brought to an open position when the actuating member of said fluid pressure actuating section has moved an amount exceeding a predetermined value; and
     an operating section for opening and closing said valve section, said operating section including a locking member for limiting the movement of said valve body.

2. An oral cavity cleaner as claimed in claim 1 wherein said operating section further comprises an operating member, said locking member engaging said operating member to lock said valve body.

3. An oral cavity cleaner as claimed in claim 2 which comprises a case; and wherein said operating member includes a knob mounted on the toothbrush side on an upper end surface of said case, said operating member being supported for sliding movement on the surface of said case, and wherein said operating member further comprises an engaging portion located at a lower end portion of said case for engaging said locking member.

4. An oral cavity cleaner as claimed in claim 2 wherein said operating member drives said valve body locking member by its sliding movement, to thereby regulate the displacement of the valve body.

5. An oral cavity cleaner as claimed in claim 2 wherein the valve body is urged by the biasing force of a spring against the pressure of the fluid from the water passage side of said actuating member.

6. An oral cavity cleaner as claimed in claim 1 wherein said pump unit comprises means for controlling the flow rate of the high-pressure fluid.

7. An oral cavity cleaner as claimed in claim 2 wherein said pump unit comprises means for controlling the flow rate of the high-pressure fluid including an operating knob for bringing the valve section to a closed position within said predetermined range, and said valve section is opened and closed by said operating member when said predetermined range is exceeded.

8. An oral cavity cleaner as claimed in claim 4 or 7 wherein said valve body is spherical in shape and said locking member is substantially arcuate in cross-sectional shape for locking the valve body by engaging its spherical surface, said valve body being released from locking engagement by rotation of said operating member through 90°.

9. An oral cavity cleaner as claimed in claim 6 wherein said flow rate control means has at least a portion thereof engaging a power source switch operating member of said pump unit.

10. An oral cavity cleaner as claimed in claim 1 wherein said flexible conduit defines a flow passage for the high-pressure fluid flowing back and forth therethrough.

11. An oral cavity cleaner as claimed in claim 1, further comprising a motion converting section including a spiral guide, said motion converting section being in engagement with said motion transmitting member or an actuating piston for converting the reciprocatory movement of said actuating piston to a swinging movement of said toothbrush.

* * * * *